US006191861B1

(12) United States Patent
McBranch et al.

(10) Patent No.: US 6,191,861 B1
(45) Date of Patent: Feb. 20, 2001

(54) FEMTOSECOND CHIRP-FREE TRANSIENT ABSORPTION METHOD AND APPARATUS

(76) Inventors: Duncan W. McBranch, 14 Sparrow La., Santa Fe, NM (US) 87501; Victor I. Klimov, 569 S. Todd Loop, White Rock, NM (US) 87544

(*) Notice: Under 35 U.S.C. 154(b), the term of this patent shall be extended for 0 days.

(21) Appl. No.: 09/249,726

(22) Filed: Feb. 13, 1999

(51) Int. Cl.[7] .................................................. G01N 21/59
(52) U.S. Cl. ........................................................... 356/432
(58) Field of Search ............................................. 356/432

(56) References Cited

U.S. PATENT DOCUMENTS 4,710,030 * 12/1987 Tauc et al. ............................ 356/432
5,706,094 * 1/1998 Maris ................................... 356/432

OTHER PUBLICATIONS

Phase Correction of Femtosecond Optical Pulses Using a Combination of Prisms and Gratings, C.H.Brito Cruz, P.C. Becker, R.L. Fork and C.V. Shank, Feb. 1988, *Optics Letters*, vol. 13, No. 2, pp. 123–125, Optical Society of America.
Picosecond Coherence Coupling in the Pump and Probe Technique, Z. Vardeny and J. Tauc, Nov. 15, 1981, *Optics Communications*, vol. 39, No. 6, pp. 396–400.
Convenient Method of Measuring the Chirp Structure of Femtosecond White–Light Continuum Pulses, Schoichi Yamaguchi and Hiro–O Hamaguchi, 1995, *Applied Spectroscopy*, vol. 49, No. 10, pp. 1513–1515.
Femtosecond White–Light Continuum Pulses, R.L. Fork, C.V. Shank, C. Hirlimann, and R. Yen, Jan. 1983, *Optics Letters*, vol. 8, No. 1, pp. 1–3.
Femtosecond Pulse Phase Measurement by Spectrally Resolved Up–Conversion: Application to Continuum Compression, Jean–Paul Foing, J.–P. Likforman, Manuel Joffre, and Arnold Migus, Oct. 1992, *IEEE Journal of Quantum Electronics*, vol. 28, No. 19, pp. 2285–2290.

* cited by examiner

Primary Examiner—Richard A. Rosenberger
(74) Attorney, Agent, or Firm—DeWitt M. Morgan (57) ABSTRACT

A method and apparatus for femtosecond transient absorption comprising phase-sensitive detection, spectral scanning and simultaneous controlling of a translation stage to obtain TA spectra information having at least a sensitivity two orders of magnitude higher than that for single-shot methods, with direct, simultaneous compensation for chirp as the data is acquired. The present invention includes a amplified delay translation stage which generates a splittable frequency-doubled laser signal at a predetermined frequency f, a controllable means for synchronously modulating one of the laser signals at a repetition rate of f/2, applying the laser signals to a material to be sample, and acquiring data from the excited sample while simultaneously controlling the controllable means for synchronously modulating.

17 Claims, 5 Drawing Sheets

FEMTOSECOND CHIRP-FREE TRANSIENT ABSORPTION METHOD AND APPARATUS

This invention was made with Government support Contract Number W-7405-ENG36 awarded by the United States Department of Energy to The Regents of the University of California. The Government has certain rights in the invention.

FIELD OF THE INVENTION

The present invention relates generally to the application of and development of transient absorption techniques, and more particularly, to a method and apparatus for femtosecond transient absorption comprising phase-sensitive detection, spectral scanning and simultaneous controlling of a time-delay translation stage resulting in highly-sensitive, chirp-free measurements of femtosecond transient absorption characteristics of a material over the entire bandwidth of a white-light and infrared continuum pulsed femtosecond light source.

BACKGROUND OF THE INVENTION

Transient absorption (TA) refers to spectral measurements of the absorption of light by a material which has first been "pumped" from its ground electronic state to an excited electronic state by a transient pulse of light (pump beam). A probe pulse of light (probe beam) then follows at some fixed delay time after the pump, and the absorption of the probe beam by the material, as a function of delay time and wavelength, yields a series of TA spectra. These spectra are useful to examine and deduce the structure of the electronic energy levels above the electronic ground state, as well as examining the mechanisms for relaxation of electrons from their excited states back down to the ground state. It is desirable to know these properties of materials, both for purposes of basic understanding, and because the operation of electronic and optical devices made from such materials often depends sensitively on these properties. For example, inorganic semiconductors such as GaAs have been widely studied using TA in order to improve the operation of devices such as diode lasers.

The most common form of prior art TA spectral measurements utilizes a chargecoupled device (CCD) camera and a spectrometer for the rapid acquisition of an entire TA spectrum at a chosen time delay. This measurement methodology is known as single-shot TA spectroscopy. However, the phenomenon known as "chirp" may greatly affect the measurement data collected. In particular, "chirp" refers to the different arrival time of different wavelengths of light within a broadband probe pulse. Chirp can arise from many sources, but the most common source is material dispersion (the term forthe phenomenon that the refractive index of materials changes as a function of wavelength of light). For example, a broadband probe pulse passing through a glass lens or window would be subjected to chirp, because the longer wavelength portions of the pulse travel faster in the material due to the lower index of refraction of glass. Prior art broadband probe pulses "continuum" beams) are generated by focusing picosecond or femtosecond pulses through a transparent material such as water, glass, or sapphire. Hence, the use of the prior art continuum generation process inherently involves creation of chirp. There is no known method for preventing chirp or for completely removing chirp from a broadband continuum (spectral width more than 200 nanometers). As a result of chirp, the delay time for a transient absorption spectrum may not be uniquely defined for every wavelength. In particular, if the delay time is less than the total chirp over the probe pulse spectral range, then the TA spectrum will be distorted by the chirp. For example, in experiments, the chirp is approximately one picosecond across the visible spectrum (450–750 nanometers). Hence, visible TA spectra are severely distorted for delay times less than 1 picosecond.

Prior art single-shot TA methodologies can be deficient for several reasons. First, as discussed above, the chirp phenomena may affect the measurements obtained. The chirp can be eliminated over a narrow spectral range by pulse compression (e.g., by using transform limited pulses). Further, transform limited pulses allow the examined spectra to remain undistorted on all time scales. However, the bandwidth for the shortest obtainable pulses (such as, for example, five femtosecond pulses) is only approximately 200 nanometers, a fraction of what is achievable with continuum generation. Therefore, broadband spectroscopy beyond the transform limit requires chirp correction. Scientists normally attempt to correct the single-shot TA chirp effect by applying numerical correction. Numerical correction requires that uncorrected spectra be taken at closely spaced time intervals and deconvolved based on the measured chirp. In using the single-shot TA methodology, a numerical correction is usually applied because the entire (chirped) spectrum is obtained. Another serious limitation to single-shot acquisition is that array detectors preclude the use of electronic noise suppression in either the frequency (lock-in detection) or the time (gated integration) domains. And, the primary obstacle in using a CCD camera is the low-frequency noise generated by the camera itself, which sets a detection limit for single-shot TA of approximately 0.2%.

The prior art measurement techniques described above are faulty for several other reasons. CCD cameras, at relatively high incident light intensities, are easily saturated by the continuum beam. Since the continuum has a strongly varying intensity with wavelength (see, e.g., FIG. 2), it is difficult to obtain TA spectra over a broad spectral range which do not either saturate the camera or result in poor signal-to-noise ratios. Further, currently available scientific-grade CCD cameras are expensive. Accordingly, as those of skill in the art will appreciate, a simple method and apparatus is desirable for measuring TA spectra which are undistorted by effects of chirp and intensity variations on the continuum probe over a broad spectral range (visible to near-infrared range) which has high sensitivity (on the order of approximately $10^{-5}$).

With the widespread availability of tunable, millijoule pulse energy, kHz repetition-rate femtosecond solid-state Ti:sapphire lasers, femtosecond transient absorption (TA) measuring techniques are now becoming the standard techniques for measuring ultra fast electronic and vibrational processes in material physics, chemistry, and biology. Unlike prior art TA measuring techniques, femtosecond chirp-free TA measuring techniques have the advantage of measuring subpicosecond energy relaxation, which is an important consideration in examining materials because it is during these short delay times that more spectral distortion occurs.

Figure 2:
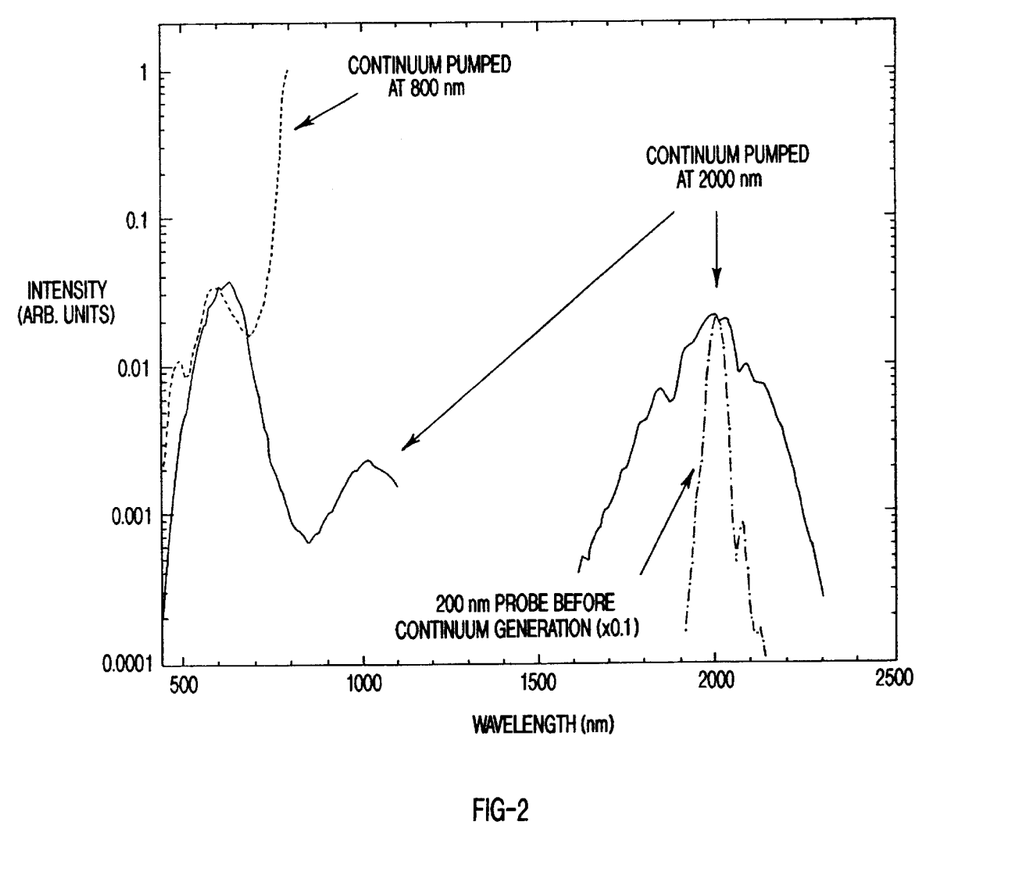
FIG. 2 is a graphical illustration of the white light and infra-red continuum beams from 450 to 2500 nanometers.

Further, phase-sensitive detection has long been a standard for measuring single wavelength pump-probe dynamics with high-repetition-rate (100-MHZ) lasers. This technique involves modulation of the intensity of the pump beam at a frequency which is lower than the repetition rate f (e.g. by using a mechanical chopper or acousto-optic or electro-optic modulator). A lock-in amplifier is then used to detect the modulation at the same frequency, which is transferred to the probe beam by the TA signal in the material. However, two modifications are necessary to optimize this technique for kilohertz repetition rate sources. First, differential amplification is necessary prior to the lock-in as it allows one to null the background signal due to the kilohertz laser pulse train, which prevents overload of the lock-in owing to insufficient dynamic reserve. The intensity variation over the continuum spectrum (as seen in FIG. 2) also makes the use of differential amplification important. In this fashion, the dynamic range is determined primarily by the photodiodes and is much greater than the range for CCD cameras. Second, synchronous modulation (chopper synchronized to exactly half the repetition rate) is necessary as it prevents phase drift between pump and chopper.

Figure 1:
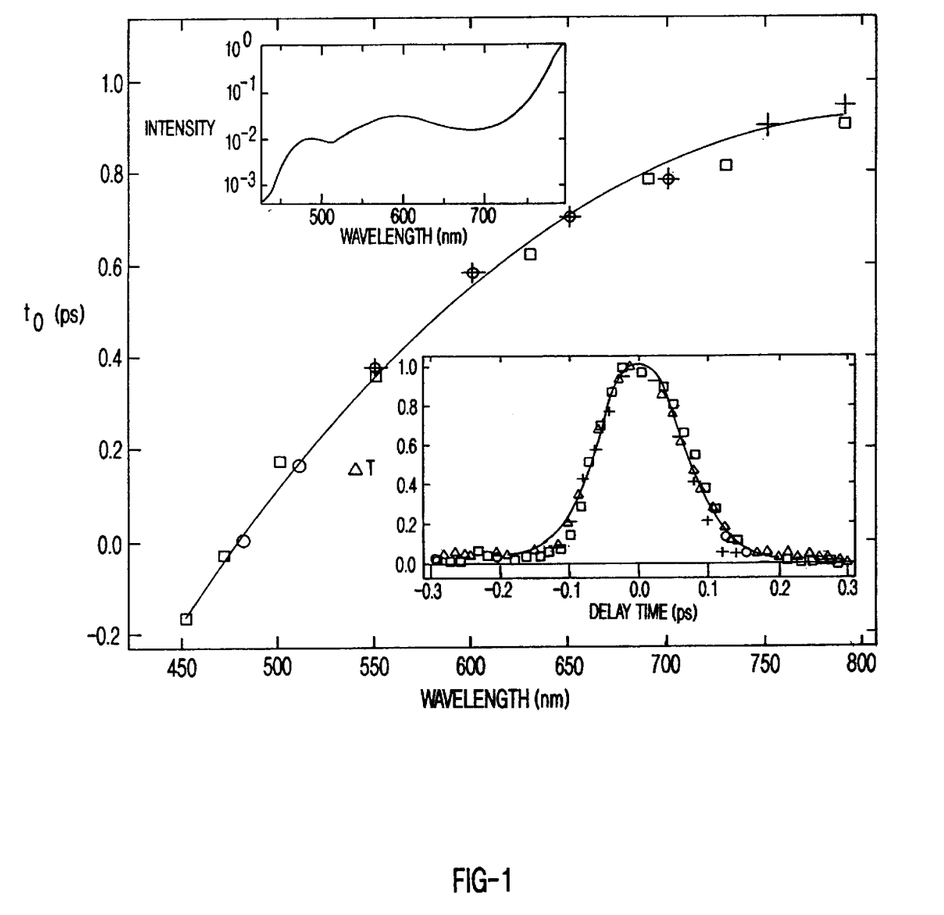
FIG. 1 illustrates the chirp effect of a probe pulse laser beam on a sample material measured by two photon absorption cross correlation with a reference pulse at 800 nanometers in one millimeter ZnS (shown as squares), 0.1 millimeter CdS (shown as crosses) or in one millimeter sapphire (shown as circles)

As is known to those of skill in the art, broadband femtosecond continuum pulses can be generated through self-phase modulation by focusing a laserthrough a transparent medium. It is possible to generate tunable probe beams at fixed wavelengths by other means (e.g. frequency-doubling, parametric generation, sum- and difference-frequency generation). However, no means are known other than continuum generation to obtain short pulses of light which simultaneously possess many different wavelengths. As such, a benefit of applying continuum pulses to TA methodologies is that they provide an opportunity to examine the energy structure of materials over a broader spectral width. In addition to the desired broad spectral width, continuum pulses have two unique characteristics uncommon to narrow band light sources. First, a continuum pulse exhibits a frequency temporal dispersion (or, chirp) as the pulse engages the material so that the red portion of the pulse arrives at an earlier time than the blue portion as described above. Second, a continuum exhibits a strong spectral non-uniformity with an intensity spike at the pump wavelength. Graphically, this is illustrated in FIGS. 1 and 2.

Accordingly, it is an object of the present invention to provide a highly sensitive, chirp-free femtosecond transient absorption spectroscopy scanning method which permits direct visualization and modeling of ultra fast, broadband energy relaxation.

It is another object of the present invention to provide a highly sensitive, chirp-free femtosecond transient absorption spectroscopy apparatus which permits direct visualization and modeling of ultra fast, broadband energy relaxation.

It is another object of the present invention to provide an apparatus which achieves highly sensitive chirp-free transient absorption spectroscopy measurements.

It is a further object of the present invention to provide a highly sensitive, chirp-free femtosecond transient absorption spectroscopy apparatus using a Tl:sapphire laser source, wherein two or more laser signals are applied to a material to be sampled for data acquisition.

It is a further object of the present invention to provide a method and apparatus for femtosecond transient absorption comprising phase-sensitive detection, spectral scanning and simultaneous controlling of a delay translation stage resulting in highly-sensitive, chirp-free measurements of femtosecond transient absorption characteristics of a material over the entire bandwidth of a white-light or infrared continuum.

Additional objects, advantages and novel features of the invention will be set forth in part in the description that follows, and in part will become apparent to those of skill in the art upon examination of the following description or may be learned by practice of the invention. The objects and advantages of the invention may be realized and attained by means of the instrumentalities and combinations particularly pointed out in the appended claims.

SUMMARY OF THE INVENTION

The present invention includes a method and apparatus for femtosecond transient absorption comprising phase-sensitive detection, spectral scanning and simultaneous controlling of a delay translation stage to obtain TA spectra information having at least a sensitivity two orders of magnitude higher than that for single-shot methods, with direct, simultaneous compensation for chirp as the data is acquired. The present invention includes an laser source which generates a series of laser pulses (pulse train) at a predetermined repetition rate which is split into two separate beams (probe and pulse), a controllable means for synchronously modulating one of the laser signals at a repetition rate of f/2, applying the laser signals to a material to be studied, and acquiring data from the excited sample while simultaneously controlling the controllable delay time of the probe beam.

DETAILED DESCRIPTION OF THE INVENTION

The present invention combines spectral scanning with phase-sensitive detection to obtain TA spectra information having a sensitivity of at least two orders of magnitude higher than that for single-shot methods, with direct, simultaneous compensation for chirp as the data is acquired.

Figure 3:
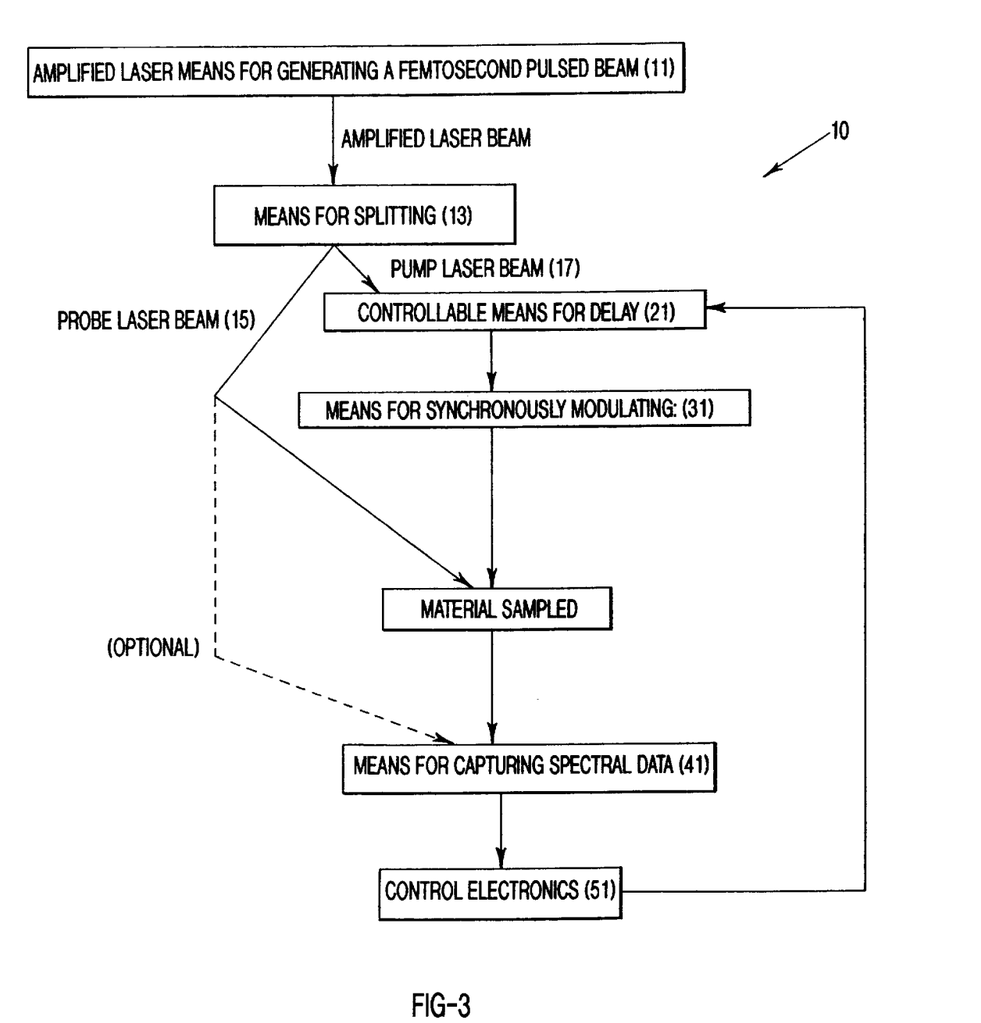
FIG. 3 illustrate several components of the present invention.

As seen graphically in FIG. 3, the present invention is a femtosecond, chirp-free transient absorption spectrometer apparatus 10 and as described further, measurement method. The present invention 10 includes a laser means 11 for generating a laser signal, controllable means for delay 21, means for synchronously modulating the laser signal 31, means for capturing spectral data 41 and control electronics 51.

Laser means 11 is a laser source which produces femtosecond or picosecond pulses having per pulse energies of 1 microjoule or greater. Preferably, this type of laser means is capable of optically generating broad-band femtosecond continuum laser pulses in a spectral range from approximately 400 nanometers to approximately 2300 nanometers. These types of laser means are available from a number of commercial manufacturers.

While more than one laser means 11 can be employed for producing multiple laser signals, it is equally beneficial and cost justified to optionally include a means for splitting 13 to split the beam produced by laser means 11 into two laser beams, a probe beam 15 and a pump beam 17 (the excitation beam). Preferably, the means for splitting 13 is an optical beam splitter/mirror with partial reflectance.

One of the beams (in the present invention, pump beam 17) must be optically routed through a controllable means for delay 21. A retroreflector, consisting of a corner-cube made of mirrors, is employed to divert the pump beam back in a direction anti-parallel to the incoming direction. The corner-cube is mounted on a translation stage which can be adjusted in small increments (0.1 micrometers) in order to change the path length which the beam must traverse before reaching the material sample. Since the pump pulse travels at the speed of light, the change in path length leads to a change in arrival time between the pump and probe (and thus, creating a delay time in arrival time). A one micrometer displacement of the translation stage leads to a 6 femtosecond round-trip additional delay time.

Pump pulse beam 17 is then optically directed towards and through the material to be sampled so that a modulating signal on the probe beam results. Probe pulse beam 15 is also directed towards and through the excited portion of the material. Optionally, the probe beam 15 can be split into another laser signal as a reference signal and optically directed to the means for capturing spectral data 41 and control electronics 51.

By employment of the controllable means for delay 21, those of skill in the art will realize that a time delay $\Delta t$ will exist between the time pulse beam 17 encounters the material compared to when probe pulse beam 15 engages the material. As seen graphically in FIG. 1, the chirp on the continuum leads to a different arrival time ($t_0$) for different spectral components of the continuum. The chirp can be measured directly by using two-photon absorption (TPA) materials as samples in the TA spectrometer. In such a TPA material, an instantaneous TA signal is observed at a given wavelength only when the pump beam and probe beam are both simultaneously present at the sample. The shape of the TPA signal as a function of delay time is shown for several wavelengths in the lower inset to FIG. 1, demonstrating a pulse width of 140 femtoseconds. In this inset, the relative delay of the peak TPA signal at different wavelengths ($t_0$) has been subtracted out to make the time scans lie on top of each other to illustrate the uniform pulse width. However, for different wavelengths, the TPA traces peak at a different delay time $t_0$ due to the chirp. Hence, a plot of $t_0$ vs. wavelength, as shown in the main panel of FIG. 1, provides a direct measurement of chirp at the sample due to all sources. The parabolic fit to this data, as shown in FIG. 1 (solid line), allows an analytical expression to be deduced to calculate $t_0$. In this way, the translation stage can be moved at each probe wavelength to correct for the chirp (e.g., to compensate for $t_0$).

Further, the ability to achieve chirp-free TA spectroscopy requires calibration of the chirp by cross correlation of the white light continuum with a reference pulse by using such techniques as frequency up conversion, two-photon absorption (TPA) or frequency-resolved optical gating. In experiments, chirp was determined from all sources by replacing the sample with a TPA material, with no other changes to the optical path. FIG. 1 shows the time position $t_0$ of the TPA maximum versus wavelength ($\lambda$) from 450 to 800 nanometers; $t_0$ corresponds to the arrival time of probe pulses at each wavelength $\lambda$. This Figure also illustrates data taken several months apart in various TPA materials. As can be seen, the chirp for a continuum generated in the single-filament regime is stable. The solid curve in this Figure is a fit to the parabolic equation $t_0 = A + B\lambda + C\lambda^2$ (where A=approximately 4.5 picoseconds, B=13.2 femtosecond/nanometer, and C=approximately $8.3 \times 10^{-3}$ femtosecond/nanometer$^2$). Chirp correction is applied at each probe $\lambda$ to obtain the same relative delay across the entire spectrum. In experiments, this correction is automated with simultaneous scanning of the monochromator and the delay stage based on the parabolic fit described above. As shown, the continuum retains a nearly transform-limited 100-femtosecond pulse width for any particular spectral window with an appropriate bandwidth. To confirm these results, the TPA calibration delay was scanned for several center wavelengths (as seen in the bottom inset of FIG. 2) using a resolution of approximately 10 nanometers. The result is a cross-correlation width of 140 femtoseconds, independent of $\lambda$.

After the pump pulse laser signal and the probe pulse signal pass through the material, the modulated probe signal from the excited material is then collected optically by a means for capturing spectral data 41. Preferably, the means for capturing spectral data 41 is a detection monochromator such as model number SP300i manufactured by Acton Research, which includes a bifurcated optical fiber bundle capable of collecting such information, followed by a silicon or HgCdTe (MCT) photodiode. This type of monochromator disperses the light into its component wavelength, for separate measurements at each wavelength, defined by the resolution of the monochromator. In application of the present invention, the wavelength is given by $\lambda \pm \Delta\lambda$, where $\Delta\lambda$ is approximately 5 nanometers.

Control electronics 51 is in electrical communication with the means for capturing spectral data 41. Control electronics 51 may include a variety of electronic control circuitry and test equipment depending on the type of analysis sought, however, in the preferred mode, control electronics 51 includes a low noise current preamplifier, a differential amplifier, a lock-in amplifier, all in electrical communication with a personal computer or like device which requires a microprocessor or microcontroller. Such a personal computer, for example, is necessary for the control of all electronic control circuitry, gathering of information, processing of information and the display of information. While prior art TA measurement techniques have utilized such components, these components were only employed individually and not in conjunction with each other.

The advantages disclosed and taught in the present invention are further explained by a discussion of the photophysics of the two representative sample materials in which excited-state features extend over the entire visible and near infrared spectrum: linear π-conjugated oligomers and semiconductor nanocrystals (NC's). In experiments for measuring femtosecond transient absorption characteristics of a material, these samples were excited at 400 nanometers by a regeneratively amplified Ti:sapphire laser signal (such as model number MXR CPA-1000 sold by Clark) set for frequency-doubled pulses (pulse width of 100 femtoseconds and a frequency rate f of 1 kHz). Before engaging the sample, the laser beam was split with an optical beam splitter into two distinct beams, a pump beam and a probe beam. Further, a continuum probe was generated in a 1-mm sapphire plate in the single-filament regime (pump energy approximately equal to 2 $\mu$). The frequency of the pump pulse beam was then modulated by a mechanical chopper synchronously at f/2. The probe pulse beam was focused with reflecting optics through the photo-excited sample. Part of the probe beam was split using a microscope cover slip to form a reference beam. It is preferable, but not critical, to also direct the reference beam through the sample.

The information relating to the probe beam (and the reference beam, if applied to the material as described above) were then collected by a means for capturing spectral data, and in particular, the dispersed beams were detected with matched large-area p-i-n Si photodiodes placed after, but in electrical communication with, an imaging monochromator having a two-leg fiber bundle. Use of these components provided sufficient spatial filtering so that no background signal due to fluorescence emission was detectable, even in highly luminescent samples. The data from the means for capturing spectral data was then electronically communicated to the control electronics for calculation and analysis of the material. As those of skill in the art will know, typical control electronics for these types of measurements include a current preamplifiers, differential amplifiers, a digital lock-in amplifier synchronized to f2 and a personal computer, all in electronic communication with one another.

This detection method taught is useful for recording chirp-free TA spectra by scanning the monochromator while simultaneously adjusting the relative pump-probe delay according to the calibrated chirp. This method yields undistorted TA spectra over the entire bandwidth of the continuum, at any time delay, limited only by the temporal resolution of the source.

As a measure of the pump-induced transmission changes, the differential transmission is applied (DT): $DT=(T-T_0)/T_0=\Delta T/T_0$, where $T_0$ and $T$ are the transmission in the absence and in the presence of the pump, respectively. $\Delta T$ is measured by chopping the pump pulse laser beam. By blocking the pump pulse laser beam and chopping the continuum probe laser beam, one can measure $T_0$ versus $\lambda$, using the same control electronics. In the small-signal limit (DT<<1), differential transmission is proportional to the pump-induced absorption changes: $DT \cong \Delta \alpha d$ (where d is the sample material's thickness). One can avoid secondary excitation of the sample by the sharply peaked continuum by choosing a fundamental wavelength $\lambda$ that is out of the range of linear absorption. To rule out TPA excitation by the probe pulse laser beam, the observed differential transmission signals must be independent of the probe pulse laser intensity.

Figure 4:
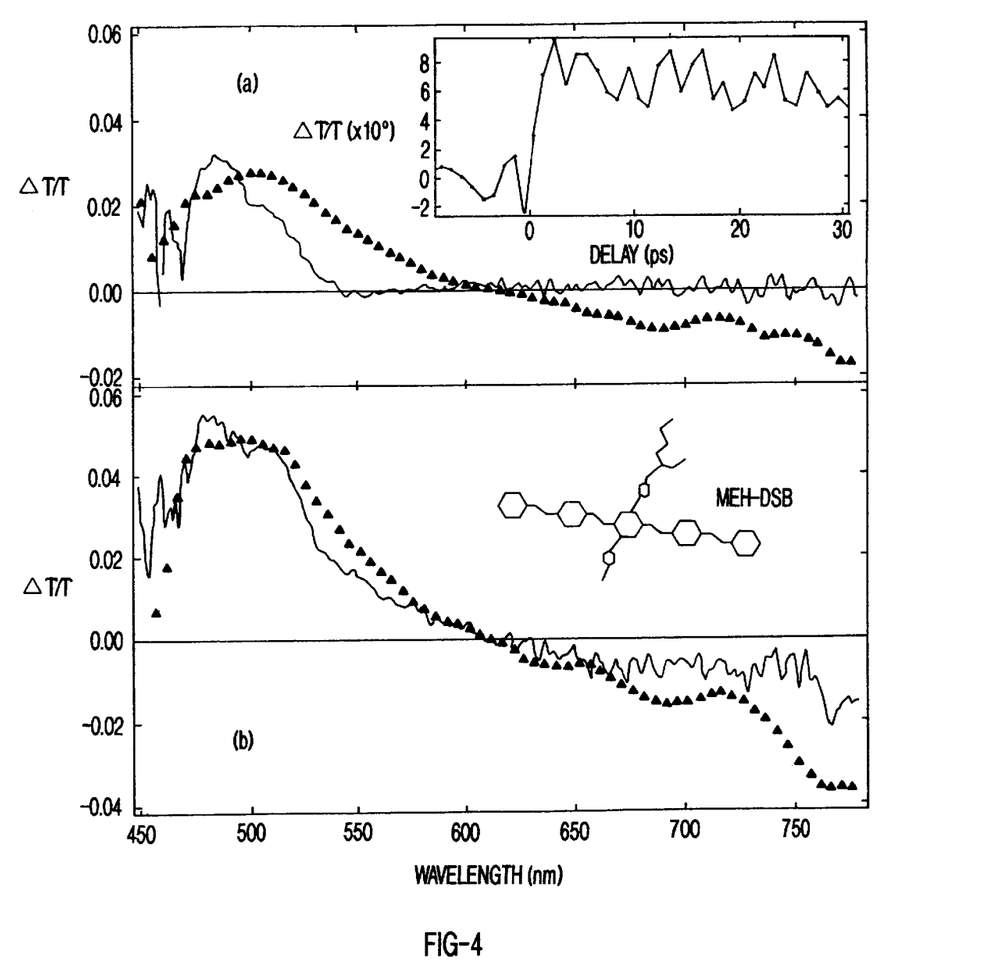
FIG. 4 illustrates the spectra of MEH-DSB measured at 300 femtoseconds and 800 femtoseconds after material excitation.

FIG. 4 illustrates a comparison of single-shot and chirp-free differential transmission spectra in the visible to near-infrared spectral region of a conjugated oligomer MEH-DSB, a model compound for highly luminescent semiconducting polymers. Single-shot spectra (solid curves) were obtained with a liquid $N_2$-cooled CCD camera by means of integrating for 0.5 s and averaging together 20 separate scans. Chirp-free spectra (triangles) were taken at intervals of 5 nanometers with a single reading of the lock-in (time constant of 0.3 second). The time delays for the two measurements match at approximately 450 nanometers. As can be seen, the single-shot differential transmission spectra for values of less than 800 femtosecond time delay are strongly distorted by the chirp. In this experiment, it is not possible to assess whether the growth dynamics of the positive (bleaching) and the negative (photo-induced absorption) differential transmission features are correlated. By contrast, from review of the chirp-free spectra, it is clear that the features arise together from the same species, namely, singlet excitons. Also, although the qualitative features are the same, the two orders of magnitude noise reduction in the chirp-free spectra enables one to distinguish subtle features on the broad excited-state absorption bands. This result highlights the effect of low-frequency noise, since data points in the single-shot spectra averaged over $10^4$ pulses, whereas chirp-free spectra data points were averaged over only 300 pulses (set by the lock-in amplifier time constant). Acquiring and processing a chirp-free differential transmission spectrum at this resolution as taught by the present invention takes approximately ten minutes due to the time required to measure each spectral data point at 5 nanometer intervals, whereas the single-shot approach requires approximately one minute. However, the dramatic improvement in the spectral data obtained justifies the additional acquisition time.

Moreover, the sensitivity attainable by use of the present invention is illustrated by a time scan in FIG. 4. In this Figure, a time scan was taken at a wavelength of 780 nanometers with a standard deviation of $1.4 \times 10^{-5}$ on a signal of magnitude $8 \times 10^{-5}$, when a pump fluence of only 25 $\mu J/cm^2$ is used. For this experiment, the lock-in time constant was set to one second and ten scans were averaged together. The sensitivity (dependent on the wavelength due to the amount of light in the continuum beam) obtained was approximately $10^{-5}$ in differential transmission near the peak of the continuum and $10^{-4}$ differential transmission in the wings. The pulse-to-pulse fluctuations on the continuum were approximately 0.5%, which is nearly independent of $\lambda$. Therefore, the sensitivity as disclosed in the present invention is only limited by laser noise. Indeed, electronic noise alone would allow at least another order of magnitude of improvement in DT. As those of skill in the art will now realize, equivalent results should be achievable with gated integration and a fast analog-digital converter in place of lock-in detection. However, in side-by-side tests using the same large area (slow) photodiodes, gated integration yielded a signal-noise ratio that was poorer by a factor of 2–5 than that obtained by use of lock-in detection.

Figure 5:
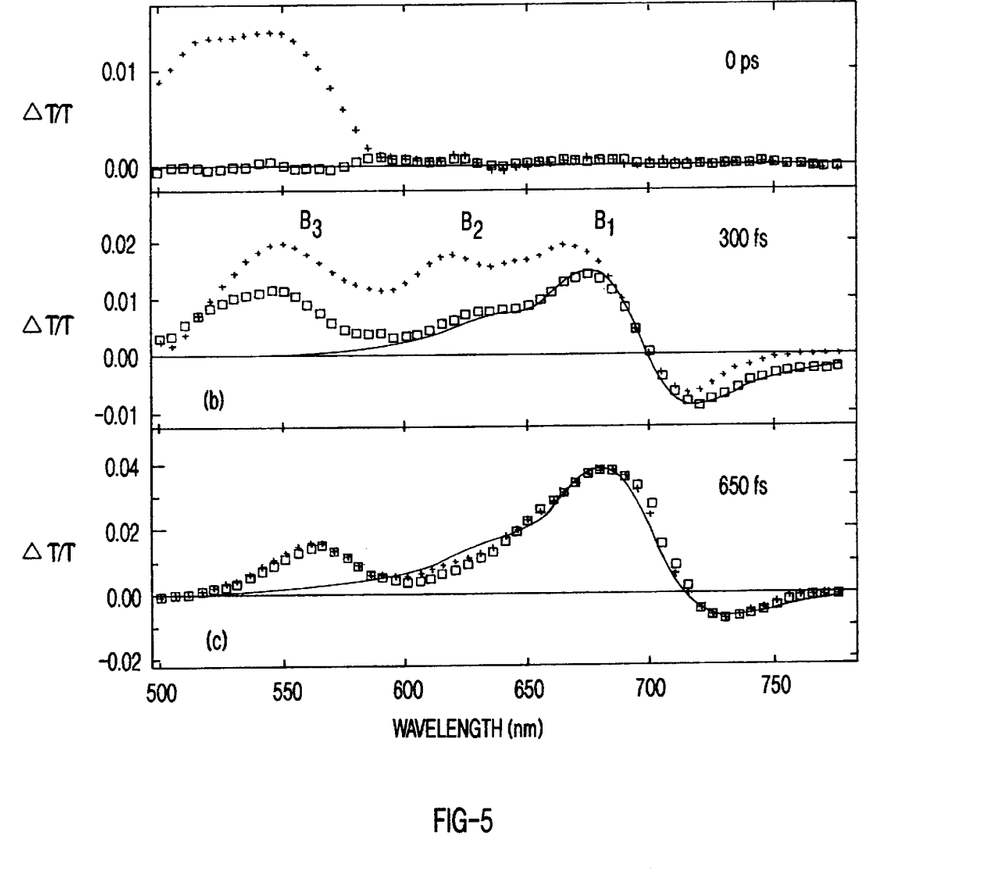
FIG. 5 is a graphical comparison of differential transmission spectra of CdSe nanocrystals measured in chirp-free scanning mode (squares) and without chirp correction (crosses).

As discussed above, the ability to recover chirp-free spectra in the first picosecond can be critical in interpreting the physics of energy relaxation. To demonstrate this quantitatively, a comparison of differential transmission spectra is taken in FIG. 5 in scanning mode with (illustrated by squares) and without (illustrated as crosses) chirp correction in CdSe NC's with an average radius of 5.6 nanometers. Three-dimensional carrier confinement in these NC's results in a discrete energy spectrum with a level spacing greatly exceeding phonon energies and a significant modification of relaxation processes relative to bulk materials.' The chirp-free differential transmission spectra provide direct information on nonequilibrium carrier energy distributions at short times following photoexcitation. During the energy relaxation, the nonlinear optical response is due to two effects: state filling-induced bleaching of the discrete optical transitions (positive differential transmission bands, labeled as items $B_1$–$B_3$ in FIG. 5) and a shift of the transitions (antisymmetric differential transmission features) caused by the internal field of the photogenerated excitons (biexciton effect). In the chirp-free spectra, despite the expected delayed population of the low-lying states, the signal appears simultaneously over the entire spectral range. The instantaneous shift of all optical transitions obscures the true carrier relaxation dynamics. A population redistribution was modeled between $B_2$ and $B_1$, taking into account both state filling and the known biexciton effect. The fits (illustrated as solid curves in FIG. 5) yield a time constant for relaxation from $B_2$ to $B_1$ of 850 femtoseconds. The corresponding electron energy loss rate was approximately 0.2 eV/ps, which is comparable with the rate for bulk CdSe, and exceeds by several orders of magnitude the expected rate owing to multiphonon emission in strongly confined systems. Hence, new ultra fast relaxation mechanisms are thus taught in strongly confined NC's, presumably from energy transfer enhanced by spatial confinement.

As those of skill in the art will appreciate, simple extensions can make the present invention's disclosed techniques even more attractive. For example, spectral detection to >1.5 μm with the long-λ continuum tail is easily accomplished with InGaAs or MCT photodiodes. As another example, higher sensitivity can be achieved with probe pulses generated by parametric amplification.

Other variations and modifications of the present invention will be apparent to those of ordinary skill in the art, and it is the intent of the appended claims that such variations and modifications be covered. The particular values and configurations discussed above can be varied, are cited to illustrate particular embodiments of the present invention and are not intended to limit the scope of the invention. It is contemplated that the use of the present invention can involve components having different characteristics as long as the principle, the presentation of a femtosecond chirp-free transient absorption method and apparatus, is followed.

What is claimed is:

1. A chirp-free method for measuring the transient absorption of a material, said method comprising the steps of:
   a. generating pulsed laser beam to serve as a pump beam;
   b. generating a broad band pulsed laser beam to serve as a probe beam, said probe beam having a spectrum of wavelengths;
   c. passing said pump beam through a means for varying the path length of said pump beam;
   d. synchronously modulating said pump beam;
   e. directing said modulated pump beam and said probe beam through said material to produce a modulated signal on said probe beam;
   f. dispersing said wavelengths of said modulated probe beam;
   g. collecting said dispersed wavelengths of said dispersed probe beam; and
   h. simultaneously compensating for chirp between different wavelengths of said dispersed probe beam by varying in a controlled manner said path length of said pump beam to maintain a substantially constant time delay between said pump beam and said different wavelengths of said probe beam.

2. The method as set forth in claim 1, further including the step of providing a single pulsed laser beam and splitting said single beam into said pump beam and said probe beam.

3. The method a set forth in claim 1, wherein said step of synchronously modulating includes blocking every other pulse of said pump beam.

4. The method as set forth in claim 1, wherein said step of directing includes the step of synchronizing said modulated pump beam and said probe beam.

5. The method as set forth in claim 1, further including the step of spectrally scanning said dispersed probe beam to collect said dispersed wavelengths of said dispersed probe beam.

6. The method as set forth in claim 5, wherein, as said dispersed wavelengths are collected, said path length of said pump beam is simultaneously adjusted.

7. The method as set forth in claim 1, wherein said substantially constant time delay is maintained by the step of adjusting the relative delay between said pump beam and said dispersed wavelengths of said probe beam according to a calibrated chirp profile.

8. The method as set forth in claim 1, further including the steps of:
   a. dividing said probe beam, before said probe beam is directed through said material, to produce an unmodulated reference beam; and
   b. performing differential amplification by subtracting said unmodulated reference beam from said probe beam after said probe beam has been modulated to null the background signal in said modulated probe beam.

9. A chirp-free transient absorption measurement apparatus, said apparatus comprising:
   a. means for generating a pulsed pump beam;
   b. means for generating a broad band pulsed probe beam, said probe beam having a spectrum of wavelengths;
   c. means, in optical communication with said pump beam, for varying the path length of said pump beam;
   d. means, in optical communication with said means for varying said path length, for synchronously modulating said pump beam;
   e. means for dispersing said wavelengths of said probe beam after said probe beam has passed through a sample being analyzed for transient absorption;
   f. means for collecting said dispersed wavelengths; and
   g. means, coupled to said means for collecting said dispersed wavelengths and said means for varying said path length, for simultaneously compensating for chirp between said different wavelengths of said dispersed probe beam to maintain a substantially constant time delay between said pump beam and said different wavelengths of said probe beam.

10. The measurement apparatus of claim 9, wherein said means for generating said pump beam and said means for generating said probe beam includes means for generating a pulsed laser beam and means for splitting said pulsed laser beam into said pump beam and said probe beam.

11. The measurement apparatus of claim 10, wherein said means for generating said pulsed laser beam is a femtosecond pulsed laser beam.

12. The measurement apparatus of claim 11 wherein said pulsed laser beam is an amplified Ti:saphire laser.

13. The measurement apparatus of claim 10, wherein said means for generating said pulsed laser beam is a picosecond pulsed laser beam.

14. The measurement apparatus of claim 9, wherein said means for varying said path length includes a retroreflector coupled to an adjustable translation stage.

15. The measurement apparatus of claim 9, wherein said means for dispersing said wavelengths of said probe beam is incorporated in a detection monochromator.

16. The measurement apparatus of claim 15, wherein said means for collecting said dispersed wavelengths is incorporated in a detector monochromator.

17. The measurement apparatus of claim 16, wherein said means for varying said path length includes a retroreflector coupled to an adjustable translation stage.

* * * * *